United States Patent
Wang et al.

(10) Patent No.: US 6,617,335 B1
(45) Date of Patent: Sep. 9, 2003

(54) PREPARATION AND DRUG COMPOSITION OF BIS-BENZYL-ISOQUINOLINE CLASS ALKALOIDS

(75) Inventors: Fengpeng Wang, Chengdu (CN); Li Wang, Chengdu (CN); Jinsong Yang, Chengdu (CN); Donglin Chen, Chengdu (CN); Xixian Jian, Chengdu (CN)

(73) Assignee: Kanghong USA, Inc., San Leandro, CA (US)

( * ) Notice: Subject to any disclaimer, the term of this patent is extended or adjusted under 35 U.S.C. 154(b) by 0 days.

(21) Appl. No.: 10/139,217

(22) Filed: May 2, 2002

(51) Int. Cl.$^7$ .................. C07D 401/02; A61K 31/47
(52) U.S. Cl. .................................. 514/308; 546/140
(58) Field of Search ........................ 546/140; 514/308

(56) References Cited

U.S. PATENT DOCUMENTS 5,025,020 A * 6/1991 Van Dyke ............... 514/280
6,124,315 A * 9/2000 Van Dyke ............... 514/308

OTHER PUBLICATIONS

Derwent Abstract of CN 1293196, Wang et al, May 2, 2001.*

Kim, H.S. et al. (1999). "Short communication: Effects of tetrandrine and fangchinoline on human platelet aggregation and thromboxane $B_2$ formation" *Journal of Ethnopharmacology* 66:241–246.

Ono, M. et al. (1994). "Positive interactions between human interferon and cepharanthin against human cancer cells in vitro and in vivo" *Cancer Chemotherapy Pharmacol.* 35:10–16.

Tian, H. and Pan, Q.–C. (Sep. 1997). "A comparative study on effect of two bisbenylisoquinolines, tetrandrine and berbamine, on reversal of multidrug resistance" *Acta Pharmaceutica Sinica* 32(4):245–250, with English abstract.

Tian, H. and Pan, Q.–C. (Sep. 1997). "Modulation of multidrug resistance by three bisbenzyl–isoquinoloines in comparison with verapamil" *Acta Pharmacologica Sinica* 18(5):455–458.

Wei, X et al. (1995) "An effective reversal agent of drug resistance in tumor cells—Study on reversal of drug resistance by tetrandrine in leukemic cells" *Acta Nanjing Med. Univ.* 15(3):543–546, and English abstract.

Wen, He Li et al. (1996). *Progress in Pharm. Sci.* 20(4):193–197.

Wiriyachita, P. and Cava, M. P. (1977). "Aromatic hydroxylation of some isoquinoline–type alkaloids" *J. Org Chem* 42(13):2274–2277.

English translation of Notice of Promulgation of Application for Inventive Patent and Entering the Substantive Inspection Procedure issued for Chinese Patent Application No. 00113166.4, Applicant: Drug research Institute of West China University of Medical Sciences, entitled "The Preparation and the Drug Composition of Bix–benzyl–isoquinoline Class Alkaloids" and Certificate of Translation dated Apr. 29, 2002, notarized by Zheng Tao.

Ames, B. N. et al. (Mar. 1973). "An improved bacterial test system for the detection and classification of mutagens and carcinogens" *Proc. Natl. Acad. Sci. USA* 70(3):782–786.

Bentley, K.W. (Apr. 1998). *The Isoquinoline Alkaloids*, Harwood Academic Publishers, Table of Contents, pp. 5–12.

Choi, H.–S. et al.(Feb. 2000). "Anti–inflammatory effects of fangchinoline and tetrandrine" *Journal of Ethnopharmacology* 69:173–179.

Fojo, A. T. et al. (Dec. 1987). "Intrinsic drug resistance in human kidney cancer is associated with expression of a human multidrug–resistance gene" *Journal of Clinical Oncology* 5(12):1922–1927.

Gottesman, M. M. and Pastan, I. (1993). "Biochemistry of multidrug resistance mediated by the mutidrug transporter" *Annual Review of Biochemistry* 62:385–427.

Gao, G. and Xiao, P. (1999). "Review of studies of bisbenzylisoquinoline alkaloid (BBI) on distrubition in higher plant and physiological activities" *Natural Product Research and Development* 11(3):96–103, with English abstract.

Kim, H. S. et al. (1997), "Vasodilating and hypotensive effects of fangchinoline and tetrandrine on the rat aorta and the stroke–prone spontaneously hypertensive rat" *Journal of Ethnopharmacology* 58:117–123.

* cited by examiner

*Primary Examiner*—Zinna Northington Davis
(74) *Attorney, Agent, or Firm*—Morrison & Foerster LLP

(57) ABSTRACT

This invention relates to the preparation of bis-isoquinoline derivatives of general formula (I) and salts thereof, which possesses multi-drug resistance (MDR) reversal activities. Drug compositions and formulations comprising bis-isoquinoline derivatives of general formula (I) and salts thereof are provided for use as sensitivity enhancers in cancer chemotherapy. Methods for inhibiting MDR by treatment with bis-isoquinoline derivatives are also provided.

12 Claims, No Drawings

PREPARATION AND DRUG COMPOSITION OF BIS-BENZYL-ISOQUINOLINE CLASS ALKALOIDS

TECHNICAL FIELD OF THE INVENTION

The invention relates to the field of isoquinoline alkaloids. Specifically, the invention relates to preparations and formulations of derivatives of bis-isoquinoline alkaloids. More specifically, the invention relates to the use of derivatives of bis-isoquinoline alkaloids with reduced toxicity in rebersing multi drug resistance (MDR) activity.

BACKGROUND OF THE INVENTION

Alkaloids are alkali-like organic compounds that form salts with acids and contain nitrogen, generally in heterocyclic and/or ring structure. Found in a wide variety of plants, alkaloids have medicinal and toxic properties. Alkaloids that possess an isoquinoline skeleton are among the most common of all alkaloids. These are derived from a 3,4-dihydroxytyramine (dopamine) precursor that undergoes a Schiff base addition with aldehydes of different origin. At least 4000 compounds of this structural type are known. The simplest type of isoquinoline alkaloids is based on carbonyl compounds such as glyoxylic acid, pyruvic acid, and an aldehyde derived from leucine. Isoquinoline alkaloids sometimes occur as dimers and oligomers. (see Isoquinoline Alkaloids, by Kenneth W. Bentley and K. W. Bentley (Gordon & Breach Publishing Group (April 1998)).

Isoquinoline alkaloids are found in plants from a wide group of genera. Plants containing isoquinoline alkaloids include the following: Argemone species (prickly poppy), Chelidonium species (celandine poppy), Corydalis species (fitweed), Dicentra species (dutchman's breeches), Papaver species (poppy), and Sanguinera species (bloodroot). Isoquinoline alkaloids are most common in the cactus family, Cactaceae, but also are found in the Chenopodiaceae, Fabaceae, Musaceae, Nympheaceae, and Sterculiaceae.

The isoquinoline alkaloids papaverine, sanguinarine, protoverine, and chelidonine are gastrointestinal (GI) tract irritants and central nervous system (CNS) stimulants. Many have varying degrees of neurologic effects, ranging from relaxation and euphoria to seizures. They are also known to cause vasodilation. About 4000 bis-benzyl-isoquinoline (BIQ) alkaloids of many important structural types are known. Many BIQ alkaloids are important in medicine. Others are highly toxic and some are used as arrow poisons. BIQ alkaloids are found in the Annonaceae, Aristolochiaceae, Berberidaceae, Eupomatiaceae, Hernandiaceae, Fabaceae, Fumariaceae, Lauraceeae, Magnoliaceae, Menispermaceae, Monimiaceae, Nelumbonaceae, Papaveraceae, Ranunculaceae, Winteraceae, Euphorbiaceae (Croton), Rhamnaceae, Phellinaceae, Symplocaceae, Rutaceae, Combretaceae, Araliaceae, Apiaceae, Caprifoliaceae, Rubiaceae, and Araceae families.

Bis-isoquinoline class alkaloids have been shown to possess a variety of biological activities (reviewed in Gao Guang Yao, Res. & Dev. Nat. Prod. (1999), 11 (3):96–103; He Li Wen et al., Progress in Pharm Sci (1996), 20(4):193–197). It has been reported that these compounds possess anti-bacterial, anti-tumor, analgesic, immunomodulator, anti-platelet agglutination, anti-arrhythmic and anti-hypertensive activities.

Natural bis-isoquinoline class alkaloids include, for example, tetrandrine, fangchinoline, etc. Fangchinoline and tetrandrine are the major alkaloids from *Stephania tetrandrae* which has been used traditionally for the treatment of inflammatory diseases in oriental countries including Korea. Both fangchinoline and tetrandrine show anti-inflammatory effects (Hong-Serck Choi, et al. Journal of Ethnopharmacology, 69(2): 173–179 (February 2000)); inhibition of platelet aggregation and thrombosis (Kim H. S., et al. Journal of Ethnopharmacology, 66(2): 241–246 (August 1999)); and effects on vasodilations and on calcium movement in vascular smooth muscle, and hypotensive effects (H. Kim, et al. Journal of Ethnopharmacology, 58(2): 117–123 (October 1997)). However, natural bis-isoquinoline class alkaloids possess significant toxic side effects.

Multiple drug resistance (MDR) mediated by the human mdr-1 gene product was initially recognized during the course of developing regimens for cancer chemotherapy (Fojo et al., 1987, Journal of Clinical Oncology 5:1922–1927). A multiple drug resistant cancer cell line exhibits resistance to high levels of a large variety of cytotoxic compounds. Frequently these cytotoxic compounds will have no common structural features nor will they interact with a common target within the cell. Resistance to these cytotoxic agents is mediated by an outward directed, ATP-dependent pump encoded by the mdr-1 gene. By this mechanism, toxic levels of a particular cytotoxic compound are not allowed to accumulate within the cell.

MDR-like genes have been identified in a number of divergent organisms including numerous bacterial species, the fruit fly *Drosophila melanogaster*, *Plasmodium falciparum*, the yeast *Saccharomyces cerevisiae*, *Caenorhabditis elegans*, *Leishmania donovanii*, marine sponges, the plant *Arabidopsis thaliana*, as well as *Homo sapiens*. Extensive searches have revealed several classes of compounds that are able to reverse the MDR phenotype of multiple drug resistant human cancer cell lines rendering them susceptible to the effects of cytotoxic compounds. These compounds, referred to herein as "MDR inhibitors", include for example, calcium channel blockers, anti-arrhythmics, antihypertensives, antibiotics, antihistamines, immuno-suppressants, steroid hormones, modified steroids, lipophilic cations, diterpenes, detergents, antidepressants, and antipsychotics (Gottesman and Pastan, Annual Review of Biochemistry 62:385–427 (1993)). Clinical application of human MDR inhibitors to cancer chemotherapy has become an area of intensive focus for research.

Recently, bis-isoquinoline class alkaloid compounds have been shown to reverse multi drug resistance (MDR). (Ye Zu Guang et al., Chin. J. Trad. Chin. Med. (1998), 23(7): 427–428; Tian Hui et al., Acta Pharmaceutica Acad Sinica (1997) 32(4):245–250; Tian Hui et al., *Acta Pharmacologica Sinica* (1997), 18(5): 455–458; Xia Wei et al., Acta Nanjing Med. Univ. (1995), 15(3):543–546; Ono M et al., Cancer Chemotherapy Pharmacol. (1994), 35(1):10–16). However, natural bis-isoquinoline class alkaloid compounds are generally toxic to humans. Also, none of these studies report any enhancer activity of these compounds with the anti-cancer agents in clinical cancer chemotherapy.

BRIEF SUMMARY OF THE INVENTION

This invention relates to methods for carrying out structural modifications of bis-isoquinoline class alkaloids. These structurally modified bis-isoquinoline class alkaloids are used as agents for reversing multiple drug resistance (MDR), especially when used as synergistic enhancers of anti-cancer drugs with improved therapeutic efficacy. The advantage of using structurally modified derivatives of bis-isoquinoline class alkaloids is that, in general, the structurally modified bis-isoquinoline class alkaloids of the invention are considerably less toxic than their natural counterparts.

This invention relates to the bis-isoquinoline class alkaloid compound of general formula (I), which is as follows:

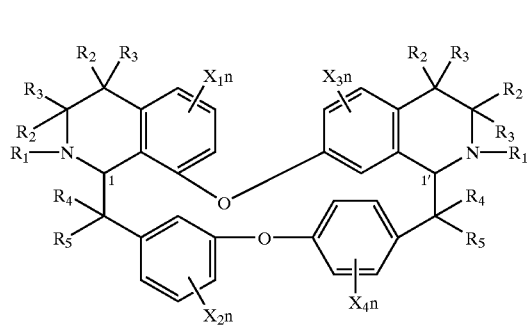

(I)

In formula (I), $R^1$ represents hydrogen, or a straight chain or branched chain alkane of 1 to 10 carbon atoms. $R^2$ and $R^3$ represent hydrogen or substituted acyl group, or straight chain or branched chain alkanes, which can be interrupted by placement of heterogeneous atoms like O, N, and S. $R^2$ and $R^3$ can also be O or S. $R^4$ and $R^5$ represent hydrogen, substituted acyl group, straight chain or branched chain alkanes or an alkane group which may be interrupted by the replacement of heterogeneous atoms like O, N, and S. $R^4$ and $R^5$ can also be O or S. $X_1$, $X_2$, $X_3$ and $X_4$ can be the same or different and also individually replaced by halogen atom or straight chain or branched chain alkaneoxy or acyloxy groups with 1 to 10 carbon atoms; and n is an integral of 1 to 4. C(1) and C(1') include all stereo isomers of RR, SS, 1S1'R and 1R1'S. The compound does not include the natural isoquinoline bis-alkaloids tetrandrine, fangchinoline, berbamine, cepharanthine and salts thereof.

In one embodiment, the invention relates to a pharmaceutical composition for administration to a patient in need thereof, comprising (a) a compound having formula (I), or a pharmaceutically acceptable salt, ester, solvate or tautomer thereof, and (b) a pharmaceutically acceptable excipient or diluent, and further comprising: (c) an anti-cancer drug in one embodiment. The anti-cancer drug may be selected from the group consisting of: microtubulin inhibitors, topoisomerase inhibitors, vinblastine, vincristine, vinorelbine, paclitaxel, docetaxel, colchicines analogs, harringtonine, homoharringtonine, camptothecine, camptothecine analogs and podophyllotoxin.

The invention also relates to an enhancer for anti-cancer chemotherapy comprising a compound having formula (I). In one embodiment, a synergistic agent for enhancing the effectiveness of one or more anti-cancer drugs comprising a compound having formula (I) is provided.

In one embodiment, the invention relates to inhibitors of multi drug resistance (MDR) comprising a compound having formula (I).

In another embodiment, the invention relates to a method for inhibiting multi drug resistance (MDR) comprising administration of an effective dose of a compound having formula (I). In one embodiment, the compound is 5-bromo-tetrandrine.

In another embodiment, the invention relates to a method for increasing the intracellular concentration of an anti-cancer drug, the method comprising administration of an effective dose of a compound having formula (I). In one embodiment, the compound is 5-bromo-tetrandrine.

DETAILED DESCRIPTION OF THE INVENTION

The efficiency of chemotherapy of tumors is seriously affected or hindered by the onset of the so called multi-drug resistance that, with respect to human tumor cells, is caused by the over expression of certain membrane bound proteins relative to normal cells. These membrane bound proteins or MDR proteins include the MDR1 protein (alternatively termed P-glycoprotein), MRP and their functional analogs. The MDR proteins extrude the applied cytostatic agents (e.g. Vinca alkaloids, anthracycline derivatives and other clinically used effective anti cancer agents) by active membrane transport to the exterior of the cell. These over expressed proteins make use of the energy obtained from ATP hydrolysis, thus making it practically impossible for the applied agents to produce their cytostatic effect.

This invention relates to the structural modifications of bis-isoquinoline class alkaloids, where the modified bis-isoquinoline alkaloids may be used as agents to reverse or inhibit multi drug resistance (MDR), especially when used as a synergistic enhancer of anti-cancer drugs, and also to improve the therapeutic efficacy of anti-cancer drugs.

This invention is based on reports that some bis-isoquinoline class alkaloids of natural origin inhibit MDR activity. In this invention, tetrandine is used as starting material to design a series of structurally modified compounds and, through animal studies and in vitro and in vivo screening of their inhibition of MDR activity, to obtain and develop a drug with more potent activity and less toxicity.

This invention further relates to formulations prepared with a compound having general formula (I) of bis-isoquinoline class alkaloids, which are used for reversal MDR active drug in the treatment of cancer as a synergistic enhancer, in order to improve chemotherapeutic efficacy.

This invention provides the following technical approaches:

Derivatives of bis-Isoquinoline Class Alkaloids

Derivatives are prepared starting with the modification by O-alkylation of phenolhydroxy group in the bis-isoquinoline class alkaloid molecule. A compound of general formula (II) is first reacted with 1% methanolic sodium-ethanol to form the phenolic sodium salt. Then alkyl-halogen is added dropwise and refluxed for a period of time, resulting in compounds with general formula of (III).

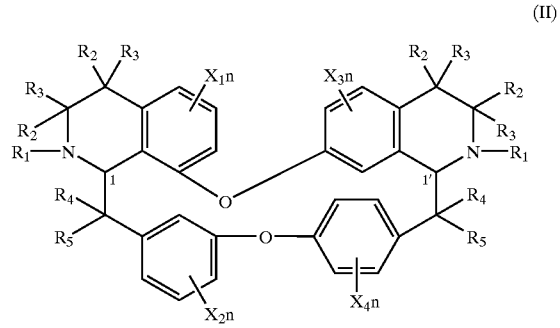

(II)

In formula (II), $R^1$ represents hydrogen, straight chain or branched chain alkyl group with 1 to 10 carbon atoms; $R^2$ and $R^3$ represent hydrogen, substituted acyl group, straight chain or branched alkyl groups which can be interrupted by the replacement of heterogeneous atoms like O, N, or S. $R^2$ and $R^3$ can also be O or S. $R^4$ and $R^5$ represent hydrogen, substituted acyl group, straight chain or branched chain alkyl groups or the alkyl group which can be interrupted by the replacement of heterogeneous atoms like O, N, or S. $R^4$ and $R^5$ can also be O or S atoms. $X_1$, $X_2$, $X_3$ and $X_4$ can be the same or different, and also individually be halogen atom or straight chain or branched chain alkyl group with 1 to 10 carbon atoms or hydroxyl, and n is an integral of 1 to 4. The compound includes all the stereo isomers of C(1) and C(1'), (RR, SS, 1S1'R and 1R1'S).

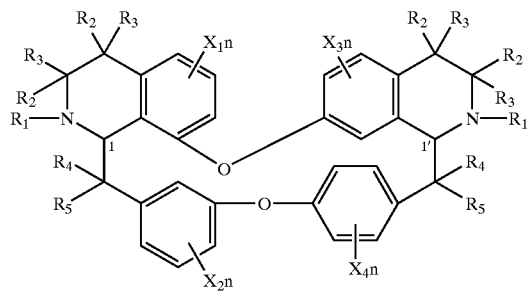

(III)

In formula (III), $R^1$ represents hydrogen, straight chain or branched chain alkyl group, with 1 to 10 carbon atoms. $R^2$ and $R^3$ represent hydrogen, substituted acyl group, straight chain or branched chain alkyl groups which can be interrupted by the replacement of heterogeneous atoms like O, N, or S. $R^2$ and $R^3$ can also be O or S. $R^4$ and $R^5$ represent hydrogen, substituted acyl group, straight chain or branched chain alkyl group, or the alkyl group which can be interrupted by the replacement of heterogeneous atoms like O, N, or S. $R^4$ and $R^5$ can also be O or S. $X_1$, $X_2$ $X_3$ and $X_4$ can be the same or different, and also individually be halogen atom or straight chain or branched chain alkyloxy, and n is an integral of 1–4; which includes all the stereo isomers of C(1) and C(1'), (RR, SS, 1S1'R and 1R1'S).

In another embodiment, derivatives may also be prepared starting with O-acylation of a phenolhydroxy bis-isoquinoline class alkaloid. Under acidic or basic conditions, compounds of formula (II) are reacted with acylating agents like acid anhydride, chloracyl compound, or mixtures thereof under anhydrous condition at ambient temperature for a couple of days, to obtain compounds with general formula (IV).

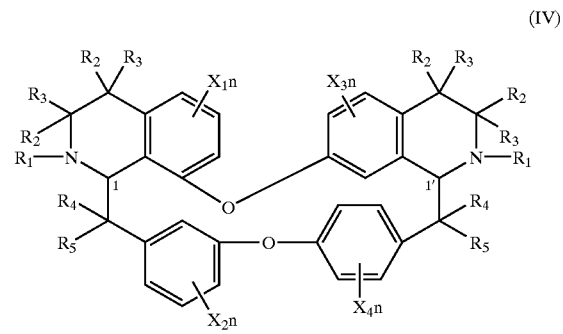

(IV)

In formula (IV), R represents hydrogen, straight chain or branched chain alkyl group with 1 to 10 carbon atoms. $R^2$ and $R^3$ represent hydrogen, substituted acyl group, straight chain or branched chain alkyl group and the alkyl group which can be interrupted by the replacement of heterogeneous atom like O, N, or S. $R^2$ and $R^3$ can also be O or S. $R^4$ and $R^5$ represent hydrogen, substituted acyl group, straight chain or branched chain alkyl group, or the alkyl group which can be interrupted by the replacement of heterogeneous atoms like O, N, or S. $R^4$ and $R^5$ can also be O or S. $X_1$, $X_2$, $X_3$ and $X_4$ can be the same or different, and also be individually replaced by halogen atom or straight chain or branched chain alkyloxy or acyloxy, and n is an integral between 1 and 4. the compound includes all the stereo isomers of C(1) and C(1'), (RR, SS, 1S1'R, and 1R1'S.

In another embodiment, derivatives may be prepared starting with the modification of the halogen substituted phenyl ring of the bis-isoquinoline class alkaloids. A compound of general formula of (V) is dissolved in a polar solvent like DMF, acetic acid-trifluoroacetic acid-water, or trifluoroacetic acid, and a halogenation agent, like N-chloro-succinimide (NCS) or N-bromo-succinimide (NBS) etc., is added dropwise. Following reaction at ambient temperature for a period of 2 to 10 hours a compound with general formula (VI) is obtained.

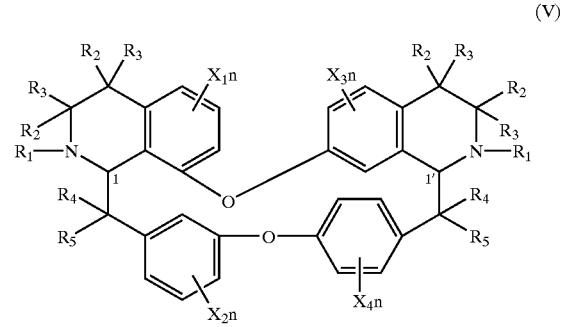

(V)

In formula (V), $R^1$ represents hydrogen, straight chain or branched chain alkyl groups with 1 to 10 carbon atoms. $R^2$ and $R^3$ represent hydrogen, substituted acyl group, straight chain or branched chain alkyl group, or the alkyl group which can be by the interrupted replacement of heterogeneous atoms like O, N, and S. $R^2$ and $R^3$ can also be O or S. $R^4$ and $R^5$ represent hydrogen, substituted acyl group, straight chain or branched chain alkyl group, or the alkyl group which can be interrupted by the replacement of heterogeneous O, N, and S. $X_1$, $X_2$, $X_3$ and $X_4$ all can be the same or different or replace by straight chain or branched chain alkyloxy or acyloxy groups with 1 to 10 carbon atoms, while n is an integer between 1 and 4. The compound includes all stereo isomers of C(1) and C(1') (namely RR, SS, 1S1'R and 1R1'S).

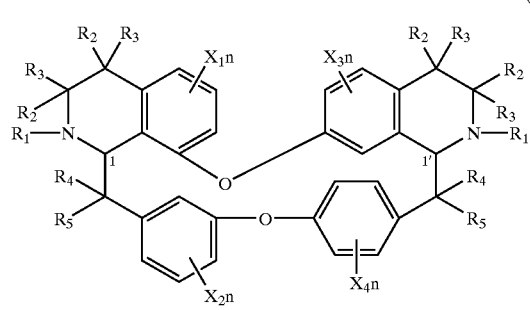

(VI)

In formula (VI), R represents hydrogen, straight chain or branched chain alkyl group with 1 to 10 carbon atoms. $R^2$ and $R^3$ represent hydrogen, substituted acyl group, straight chain or branched chain alkyl group and the alkyl group which can be interrupted by the replacement of heterogeneous atoms like O, N, and S. $R^2$ and $R^3$ can also be O or S. $R^4$ and $R^5$ represent hydrogen, substituted acyl group, straight chain or branched chain alkyl groups, and the alkyl group which can be interrupted by the replacement of heterogeneous atoms like O, N, and S. $R^4$ and $R^5$ can also be O or S. $X_1$, $X_2$, $X_3$ and $X_4$ can be the same or different, or individually replaced by halogen atom, or substituted by straight chain or branched chain acyloxy group, and n is an integer between 1 and 4. At the same time it includes all stereo isomers of C(1) and C(1') (namely RR, SS, 1S1'R and 1R1'S).

According to the invention, preparation of compounds including and similar to the above-mentioned modified structures can be performed starting with various kinds of natural bis-isoquinoline class alkaloids, for instance, tetrandrine, fangchinoline, etc. The invention provides a simple, convenient method and can be scaled up for mass production in an industrialized setting.

Wiriyachita P and Cava M P (J. Org Chem (1977), 42:2274–2277) used similar synthetic methods to prepare a compound according to general formula (I) having the formula (VII). However, Wiriyachita and Cava do not mention any MDR reversal activity and do not disclose use of the compound (VII) as a synergistic enhancer of anti-cancer drugs.

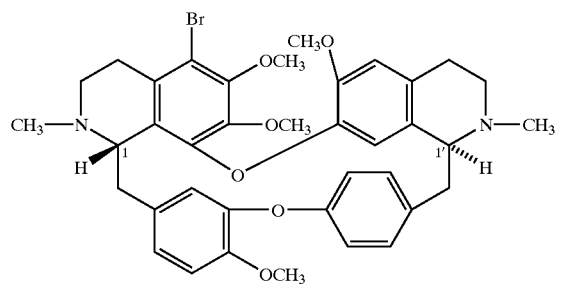

(VII)

Examples of compounds of the invention with the general formula (I) are described below in Examples 1 through 21.

According to methods described in this invention, compounds with the general formula (I) possess the property of reversing MDR activity. As shown in experiments described in Examples 1 through 21, the compounds could significantly increase the sensitivity of vinblastine against the multi drug resistance cell line of P388/adr at levels of 0.1 µg/mL in vitro. The $IC_{50}$ value was in the range of 2–3 µg/mL, the reversal index against P388 was around 20, and most of the compounds completely reversed multi drug resistance of vinblastine-treated tumor cells. In a comparative experiment with the compound cepharanthine (compound VIII), the $IC_{50}$ value was 11.7 µg/mL which means that the compounds in this invention are more potent than cepharanthine (VIII).

As shown in Example No. 8, in a nude mice xerografted with P338/adr experiments, the compounds of the invention displayed significantly stronger inhibition of MDR activity of vinblastine against P388/adr than cepharanthine (VIII), resulting in an increase of survival rates by the combined therapy by 37.7%.

An isotopic determination of vinblastine concentrations in P399/adr MDR cell lines revealed that vinblastine concentrations in the combined therapy group were significantly higher than those using vinblastine monotherapy, and also higher than those using other known inhibitors of MDR activity like, tetrandrine, fangchinoline, cepharanthine etc. Inhibition of MDR activity by a compound of the invention was comparable to the available agent verapamil, but acute toxicity levels of the compound ($LD_{50}$>125 mg/kg) was much lower than that of verapamil ($LD_{50}$=8 mg/kg). (see Example No. 8)

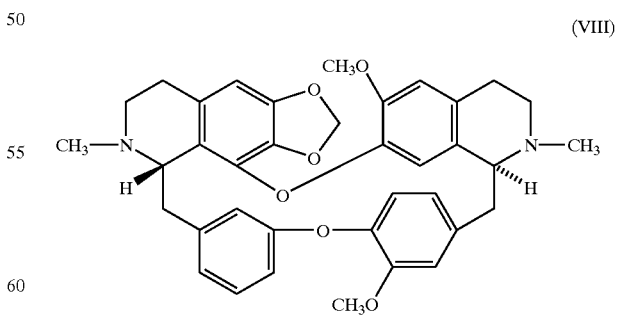

(VIII)

Formulations Comprising Compounds of Formula (I)

This invention also relates to the preparation of the general formula compound (I) with suitable auxiliaries and excipients. The formulations are for use in reversing MDR activity. In one embodiment they are used in conjunction with anti-cancer therapy.

The methods of treatment provided by this invention are practiced by administering to a patient in need thereof, a dose of a compound of the general formula (I), or a pharmaceutically acceptable salt, ester, solvate or tautomer thereof. In another aspect, the novel compounds used to practice this invention are set forth above. Using a method of the invention, therapeutic compounds are typically administered to human patients topically to the skin or mucous membranes, by extra-ocular application, intraocularly (by chemical delivery system or invasive device), or systemically (e.g. sublingually, by suppository, by oral ingestion, intradermally, by inhalation, intramuscularly, intra-articularly, intravenously, or other parenteral route). Parenteral administration by a particular route is used in appropriate circumstances apparent to the practitioner. Oral administration is the preferred route for chronic diseases. Topical administration is the preferred route for dermatological diseases. Extra-ocular application is the preferred route for ocular diseases involving the anterior segment of the eye, or chronic diseases Preferably, the compositions are administered in unit dosage forms suitable for single administration of precise dosage amounts.

In embodiments of this invention, formulations of compounds of the general formula (I) can be prepared as an ointment, gel, paste, cream, spray, lotion, suspension; solute or emulsion in aqueous or non-aqueous solvents or, syrup, granules or powder.

The compounds (I) and their salts can be further processed to galenical formulations such as, ointment, salve, tablet, capsule, suppository, emulsion, infusion and injection in a compounding method using known additives and excipients for administration by local, oral and parenteral routes.

Compounds of the general formula (I) can be processed into tablet, lozenge, capsule, pill and injection forms when formulated with the following components or similar components thereof:

(a) filling agent: starch, sugar and silicic acid;

(b) binder: cellulose derivatives, alginates, gelatin, and polyvinyl-pyrrolidone (PVP);

(c) wetting agent: glycerine;

(d) disintegrating agent: agar, calcium carbonate, sodium bicarbonate;

(e) absorption accelerant: quaternary compounds;

(f) surface active agent: hexadecanol;

(g), absorption carrier: kaolin, bentonite;

(h) lubricant: talc, calcium or magnesium stearate, carbowax (solid);

(i) pH adjusting agent: HCl, Sodium bicarbonate, Sodium hydroxide;

(j) isotonic agent: citric acid, sodium citrate, lactic acid, sodium lactate;

(k) cosolvent: Nipagin, ethylparaben, Tween-80

(l) antioxidant: Sodiumpyroslfite, sodium sulfo-sulfate, sodium sulfite, ascorbic acid For oral administration, enteric or encapsulated formulations such as tablet, capsule, lozenge and pill may be used. Encapsulation is usually done by polymers or waxes to protect the ingredients and screen from light, and formulated to dissolve the capsular material at or adjacent a target organ in order to concentrate the action of the compounds in the target organs. The active ingredients can also be processed by using the above-mentioned diluents to become microencapsulation preparation. The compound can be processed by using standard techniques known in the art, singly or formulated with specific diluents/excipients and/or other drugs.

A preferred dosage of compound (I) is in the range of 0.0001 to 5 mg/kg body weight with an optimum range within 0.01 to 5 mg/kg body weight.

The experimental studies described below showed that inhibition of MDR activity of compounds and their salts with general formula (I) can increase the efficacy of anti-cancer chemotherapy. Also compound (I) could be used as a sensitivity enhancing agent in anti-cancer chemotherapy.

It was also shown in the experimental studies, that the compounds and their salts with general formula (I) could increase the sensitivities of the anti-cancer drugs when used in combination with those of having mode of actions like microtubulin inhibitors and topoisomerase inhibitors, e.g. vinblastine, vincristine, vinorelbine, paclitaxel, docetaxel, colchicines analogs, harringtonine, homoharringtonine, camptothecine analogs, podophyllotoxin, etc.

Activity of Compounds of the Formula (I)

Experimental studies using a product, 5-bromotetrandrine, of formula (I) showed following results (the compound is described in Example 8 below):

1. In Vivo Study of Inhibition of MDR Activity of the Compound

Method: Using defined characteristics of human leukemia P388/adr cell line in a nude mice model to determine the inhibition of MDR activity. Quantitative subcutaneous injection of P388 cell into the armpit of nude mice was followed for a certain period of time. When the tumor started growing, the animals were divided in 5 groups (n=5) and treated with vincristine (monotherapy), vincristine plus the compound in high, middle and low doses (combined therapy), and cepharanthine plus the compound (combined therapy). The formulations and a cepharanthine control were administered by intraperitoneal injection for 2 to 4 times a day, and the animals consecutively observed for 10 days. Life span and survival rates were calculated.

Results: In combined therapy with a compound of general formula VII, the survival rates of xenografted nude mice were extended by 37.7%, significantly longer than the monotherapy group animals.

2. Isotopic Determination of Vincristine Concentration in the P388/adr Cell Line Method: By using an isotope marker, differences were observed between intracellular vincristine concentrations during combined therapy and single therapy. The results were also compared with known inhibitors of MDR activity like cepharanthine, tetrandrine, fangchinoline and verapamil combination. The dosages were arranged in low, middle and high groups in parallel studies, results were calculated in dpm of vincristine concentration in the cell.

Results obtained with the compound in Example 8 revealed that the isotope marker concentration of vincristine in the P338/adr of combined therapy groups, with three levels corresponding to verapamil; yet significantly higher than the other control groups.

3. Acute Toxicity Levels

Method: $LDs_{50}$ values for the compounds of formula (I) were calculated according to the method of Gaddum and Gu Han Yi.

For the compound of Example 8, administered by intravenous and intraperitoneal administrations in one month, the $LDs_{50}$ were >125 mg/kg bodyweight and >368 mg/kg bodyweight respectively.

4. Mutagenicity Test (Ames Method):

Determinations were carried out the using *Salmonella typhimurium* histamine deficiency mutants types TA97, TA98, TA100 and TA102 to detect the mutagenicity of said compound. Mutagenicity was determined according to the method of Ames. (Ames, B., et al. (1973). An improved bacterial test system for the detection and classification of mutagens and carcinogens. *Proc. Natl. Acad. Sci. USA* 70: 782–786). In the plate method with dosages of 100, 20, 4, 0.8, and 0.16, compared with the blank control, (self made compound S9), counting the number of reversed mutative colony changed, to decide the mutagenicity of the test compound.

Results showed that the compound was void of mutagenicity.

EXAMPLES

The following examples are provided for further clarification of the invention illustrative of compounds described in this invention. These are neither intended to restrict the scope of the compounds according to the invention, nor intended to restrict the technical approaches described in this invention, in order to readily prepare compounds with the general formula (I). Alternative or modified protocols for preparation of the compound described in this invention, can be readily formulated by ordinary technicians in the field.

Example 1

(1)

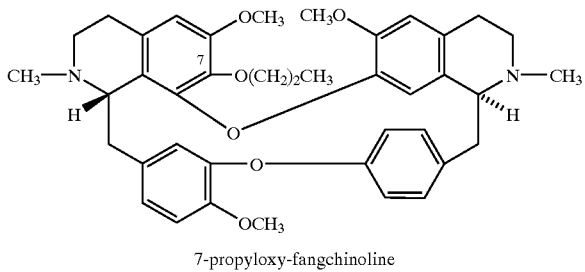

7-propyloxy-fangchinoline

Protocol: 0.16 mole of fangchinoline was weighed into an Erlenmeyer flask, and 10 mL anhydrous ethyl alcohol was added. the mixture was stirred to dissolve at room temperature, and 2 mL of 1% NaOH ethanolic solution was added dropwise. Stirring was continued, then refluxed by heating for 1 hour, and 0.35 mol of ethanolic n-bromopropane was added dropwise, and further refluxed for another 4 hours. The solvent was removed by filtration and a light yellow substance was obtained. The compound was purified either by column chromatography or recrystallization in methanol or ethyl ether.

Yield: 75%; Colorless needle crystalline (in methanol), m.p.: 175–176° C.; $C_{40}H_{46}N_2O_6$; FAB/MS m/z (%): 651 (M+1, 100), 73 (99); IR (in KBr max): $cm^{-1}$: 1582; $^1$HNMR (200 MHz, $CDCl_3$) δ: 0.65 (t, J=7.2 Hz, $OCH_2CH_2CH_3$), 2.31 (s, $NCH_3$), 2.58 (s, N'—$CH_3$), 3.35 (s, 6'-$OCH_3$), 3.72 (s, 6-$OCH_3$), 3.91 (s, 12-$OCH_3$), 5.94 (s, 8'-H), 6.29 (s, 5-H), 6.30 (dd, J=8.0, 2.0 Hz, 10'-H), 6.49 (s, 5'-H), 6.50 (s, 10-H), 6.81 (dd, j=8.0, 2.3 Hz, 11'H), 6.86 (s, 13-H), 6.91 (br.s, 14-H), 7.13 (dd, J=8.0, 2.4 Hz, 13'-H), 7.36 (dd, J=8.0, 2.1 Hz, 14'-H). $^{13}$CNMR (75 MHz, $CDCl_3$) δ: 61.4 (1), 44.2 (3), 22.1 (4), 127.3 (4a), 105.8 (5), 151.4 (6), 136.9 (7), 148.4 (8), 122.7 (8a), 134.6 (9), 115.9 (10), 149.3 (11), 147.0 (12), 111.4 (13), 122.7 (14), 41.8 (15), 64.4 (1'), 45.4 (3'), 24.1 (4'), 127.3 (4a'), 112.7 (5'), 148.6 (6'), 143.8 (7'), 120.1 (8'), 127.8 (8a'), 134.9 (9'), 132.6 (10'), 121.9 (11'), 153.7 (12'), 121.9 (13'), 130.1 (14'), 40.9 (15'), 42.3 (N—$CH_3$), 42.4 (N'—$CH_3$), 55.7 (6-$OCH_3$), 55.8 (6'-$OCH_3$), 56.1 (12-$OCH_3$), 74.3 t, 21.6 t, 160.1 q (7-$OCH_2CH_2CH_3$).

The following compounds were prepared by methods similar to that in Example 1:

Example 2

(2)

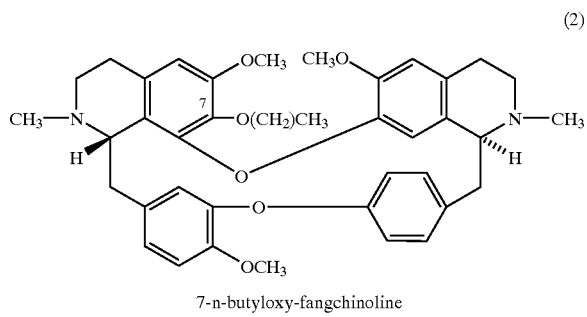

7-n-butyloxy-fangchinoline

Yield: 56%; Colorless prism crystal (in Methanol); m.p. 155–156°; $C_{41}H_{48}N_2O_6$; FAB-MS: m;z (%): 665 (M+1, 100). $^1$HNMR (200 MHz, $CDCl_3$) δ: 2.32 (s, N—$CH_3$), 2.60 (s, N'—$CH_3$), 3.35 (s, 6'-$OCH_3$), 3.72 (s, 6-$OCH_3$), 3.92 (s, 12-$OCH_3$), 5.94 (s, 8'-H), 6.29 (s, 5-H), 6.30 (dd, J=7.6, 2.2 Hz, 10'-H), 6.49 (s, 5'-H), 6.51 (d, j=1.4 Hz, 10-H), 6.81 (dd, j=8.0, 2.2 Hz, 11'-H), 6.86 (s, 13-H), 6.91 (br.s, 14-H), 7.13 (dd, J=8.0, 2.2 Hz, 13'-H), 7.36 (dd, J=8.1, 2.1 Hz, 14'-H), 1.12(t, j=7.2 Hz, 7-$OCH_2$—$CH_2$—$CH_3$). $^{13}$CNMR (75 MHz, $CDCl_3$) δ: 61.4 (1), 44.2 (3), 22.0 (4), 127.4 (4a), 105.8 (5), 151.4 (6), 136.0 (7), 148.4 (8), 122.7 (8a), 134.6 (9), 115.9 (10), 149.3 (11), 146.9 (12), 111.4 (13), 122.7 (14), 41.8 (15), 64.4 (1'), 45.8 (3'), 24.2 (4'), 127.8 (4a'), 112.7 (5'), 148.6 (6'), 143.8 (7'), 120.0 (8'), 127.9 (8a'), 135.0 (9'), 132.5 (10'), 121.9 (11'), 153.6 (12'), 121.8 (13'), 130.1 (14'), 40.9 (15'), 42.2 (N—$CH_3$), 42.5 (N'—$CH_3$), 55.7 (6-$OCH_3$), 55.8 (6'-$OCH_3$), 56.0 (12-$OCH_3$), 72.5 t, 31.3 t, 18.8 q, 13.8 q (7-$OCH_2CH_2CH_2CH_3$).

Example 3

(3)

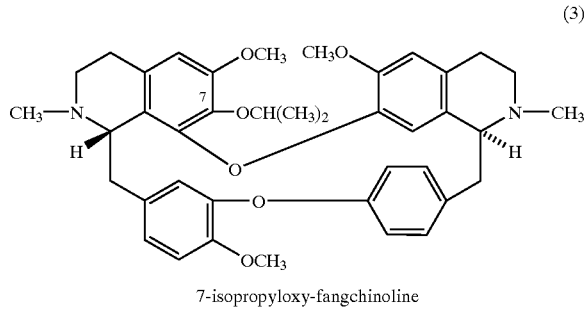

7-isopropyloxy-fangchinoline

Yield: 36% A white amorphous powder; $C_{40}H_{46}N_2O_6$; FAB/MS m/z (%): 651 (M+1, 87); IR (in KBr max): $cm^{-1}$: 1581. $^1$HNMR (200 MHz, $CDCl_3$) δ: 2.34 (s, N—$CH_3$), 2.62

(s, N'—CH$_3$), 3.34 (s, 6'-OCH$_3$), 3.71 (s, 6-OCH$_3$), 3.92 (s, 12-OCH$_3$), 5.86 (s, 8'-H), 6.30 (s, 5-H), 6.33 (dd, J=8.4, 2.2 Hz, 10'-H), 6.50 (br.s, 5'-H), 6.50 (br.s, 10-H), 6.83 (dd, j=8.4, 2.4 Hz, 11'-H), 6.86 (d, j=8.0 Hz, 13-H), 6.95 (br.s, 14-H), 7.14 (dd, J=8.0, 2.4 Hz, 13'-H), 7.38 (dd, J=8.2, 2.0 Hz, 14'-H), 0.73[d, j=6.0 Hz, 7-OCH(CH$_3$)$_2$]. $^{13}$CNMR (75 MHz, CDCl$_3$) δ: 61.6 (1), 44.6 (3), 22.3 (4), 126.5 (4a), 105.3 (5), 151.9 (6), 134.8 (7), 148.6 (8), 122.2 (8a), 134.2 (9), 115.6 (10), 149.3 (11), 147.0 (12), 111.4 (13), 122.8 (14), 41.7 (15), 64.5 (1'), 45.1 (3'), 23.6 (4'), 127.1 (4a'), 112.7 (5'), 148.8 (6'), 143.3 (7'), 120.0 (8'), 127.7 (8a'), 134.6 (9'), 132.5 (10'), 121.9 (11'), 153.6 (12'), 121.9 (13'), 130.1 (14'), 40.8 (15'), 42.2 (N—CH$_3$), 42.4 (N'—CH$_3$), 55.5 (6-OCH$_3$), 55.7 (6'-OCH$_3$), 56.0 (12-OCH$_3$), 73.9 dt, 21.2 q [7-OCH(CH$_3$)$_2$].

Example 4

(4)

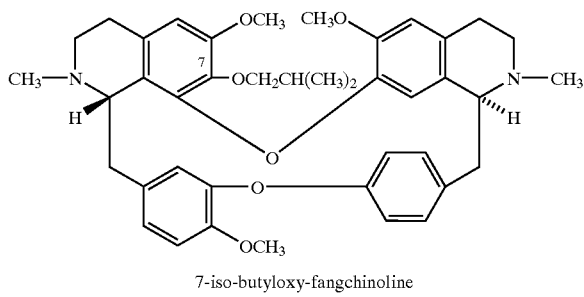

7-iso-butyloxy-fangchinoline

Yield: 38%. A white amorphous powder; C$_{41}$H$_{48}$N$_2$O$_6$; FAB/MS m/z (%): 665 (M+1, 100). $^1$HNMR (200 MHz, CDCl$_3$) δ: 2.34 (s, N—CH$_3$), 2.61 (s, N'—CH$_3$), 3.36 (s, 6'-OCH$_3$), 3.72 (s, 6-OCH$_3$), 3.92 (s, 12-OCH$_3$), 5.96 (s, 8'-H), 6.31 (s, 5-H), 6.31 (dd, J=8.2, 1.8 Hz, 10'-H), 6.50 (s, 5'-H), 6.50 (s, 10-H), 6.81 (dd, j=8.2, 2.2 Hz, 11'-H), 6.85 (d, j=8.2 Hz, 13-H), 6.91 (br.s, 14-H), 7.13 (dd, J=8.2, 2.2 Hz, 13'-H), 7.38 (dd, J=8.2, 2.0 Hz, 14'-H), 0.65[d, j=6.6Hz, 7-OCH$_2$CH(CH$_3$)$_2$]. $^{13}$CNMR (75 MHz, CDCl$_3$) δ: 61.5 (1), 44.4 (3), 22.1 (4), 126.9 (4a), 106.2 (5), 151.4 (6), 137.4 (7), 148.2 (8), 122.6 (8a), 134.3 (9), 115.8 (10), 149.2 (11), 147.0 (12), 111.4 (13), 122.8 (14), 41.7 (15), 64.4 (1'), 45.5 (3'), 23.9 (4'), 127.5 (4a'), 112.8 (5'), 148.5 (6'), 144.1 (7'), 120.2 (8'), 127.6 (8a'), 134.6 (9'), 132.5 (10'), 121.8 (11'), 153.7 (12'), 121.8 (13'), 130.1 (14'), 41.3 (15'), 42.3 (N—CH$_3$), 42.3 (N'—CH$_3$), 55.8 (6-OCH$_3$), 55.8 (6'-OCH$_3$), 56.0 (12-OCH$_3$), 79.2 dt, 28.4 d, 19.1 q[7- OCH$_2$CH(CH$_3$)$_2$].

Example 5

(5)

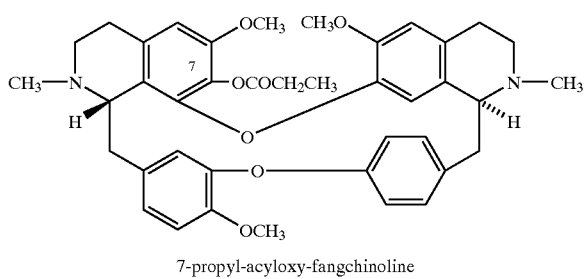

7-propyl-acyloxy-fangchinoline

Protocol: 0.16 mole of fangchinoline was weighed out into an Erlenmeyer flask, 0.12 mole of propionic anhydride was added, stirred to dissolve, stirring continued for 3 hours at 40° C., and the solvent filtered. A white color powder was obtained and the product was collected by column chromatography, or by crystallization in acetone-ethyl ether mixture.

Yield: 60% as a white amorphous powder. C$_{40}$H$_{44}$N$_2$O$_7$; FAB/MS m/z (%): 665 (M+1, 40). $^1$HNMR (200 MHz, CDCl$_3$) δ: 2.37 (s, N—CH$_3$), 2.61 (s, N'—CH$_3$), 3.40 (s, 6'-OCH$_3$), 3.69 (s, 6-OCH$_3$), 3.91 (s, 12-OCH$_3$), 5.94 (s, 8'-H), 6.34 (s, 5-H), 6.24 (dd, J=8.1, 2.3 Hz, 10'-H), 6.46 (s, 5'-H), 6.51 (s, 10-H), 6.78 (dd, j=8.4, 2.2 Hz, 11'-H), 6.84 (d, j=8.2 Hz, 13-H), 6.94 (br.s, 14-H), 7.11 (dd, J=8.0, 2.4 Hz, 13'-H), 7.32 (dd, J=8.2, 2.0 Hz, 14'-H), 0.89[d, j=7.6Hz, 7-OCOCH$_2$CH$_3$]. $^{13}$CNMR (75 MHz, CDCl$_3$) δ: 61.2 (1), 44.0 (3), 21.9 (4), 127.8 (4a), 105.6 (5), 149.8 (6), 142.7 (7), 147.2 (8), 122.3 (8a), 134.5 (9), 116.1 (10), 149.3 (11), 147.0 (12), 111.5 (13), 122.7 (14), 40.2 (15), 64.0 (1'), 45.3 (3'), 24.5 (4'), 128.6 (4a'), 112.4 (5'), 148.6 (6'), 134.6 (7'), 120.4 (8'), 130.2 (8a'), 134.6 (9'), 132.4 (10'), 122.2 (11'), 153.8 (12'), 121.9 (13'), 130.6 (14'), 41.5 (15'), 42.2 (N—CH$_3$), 42.3 (N'—CH$_3$), 55.5 (6-OCH$_3$), 55.9 (6'-OCH$_3$), 56.0 (12-OCH$_3$), 170.9 s, 26.0 t, 8.6 q[7-OCOCH$_2$CH$_3$].

Example 6

(6)

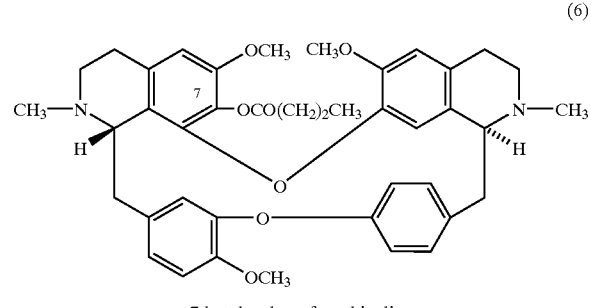

7-butylacyloxy-fangchinoline

Yield: 81%; A white amorphous powder C$_{41}$H46N$_2$O$_7$; FAB/MS m/z (%): 665 (M+1, 40); IR (in KBr max): cm$^{-1}$: 1761. $^1$HNMR (200 MHz, CDCl$_3$) δ: 2.36 (s, N—CH$_3$), 2.60 (s, N'—CH$_3$), 3.40 (s, 6'-OCH$_3$), 3.69 (s, 6-OCH$_3$), 3.91 (s, 12-OCH$_3$), 5.93 (s, 8'-H), 6.34 (s, 5-H), 6.24 (dd, J=8.1, 2.3 Hz, 10'-H), 6.46 (s, 5'-H), 6.50 (s, 10-H), 6.79 (dd, j=8.2, 2.4 Hz, 11'-H), 6.84 (d, j=8.0 Hz, 13-H), 6.92 (br.s, 14-H), 7.10 (dd, J=8.0, 2.6 Hz, 13'-H), 7.32 (dd, J=8.2, 2.0 Hz, 14'-H), 0.84[d,j=7.2Hz, 7-OCO(CH$_2$)$_2$CH$_3$]. $^{13}$CNMR (75 MHz, CDCl$_3$) δ: 61.0 (1), 43.7 (3), 21.9 (4), 127.8 (4a), 105.4 (5), 149.6 (6), 142.5 (7), 147.0 (8), 122.4 (8a), 134.6 (9), 116.0 (10), 149.1 (11), 146.8 (12), 111.3 (13), 122.5 (14), 41.4 (15), 63.9 (1'), 45.5 (3'), 24.8 (4'), 128.8 (4a'), 112.3 (5'), 148.4 (6'), 134.7 (7'), 120.3 (8'), 139.9 (8a'), 134.7 (9'), 132.3

(10'), 121.8 (11'), 153.6 (12'), 121.7 (13'), 130.5 (14'), 39.8 (15'), 42.0 (N—CH$_3$), 42.5 (N'—CH$_3$), 55.4 (6-OCH$_3$), 55.7 (6'-OCH$_3$), 55.9 (12-OCH$_3$), 169.9 s, 34.5 t, 17.7 t, 13.2q [7-OCO(CH$_2$)$_2$CH$_3$].

Example 7

(7)

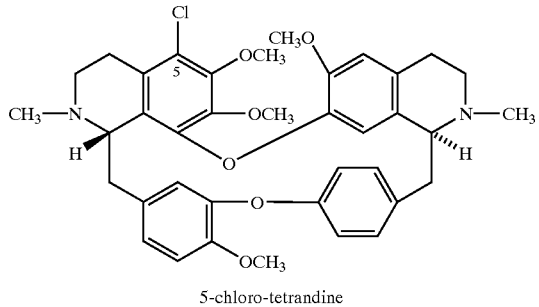

5-chloro-tetrandrine 0.16 mole of tetrandrine was weighed into an Erlenmeyer flask, 2 mL of trifluoro-acetic acid at 0° C. was added, stirred to dissolve, 0.16 mole of N-chloro-succinimide was added by aliquot, stirred and raised to room temperature and continued to react for another 7 hours. A white solid substance was obtained and purified by column chromatography or crystallization with methanol. A white amorphous crystalline compound was isolated.

Yield: 75% C$_{38}$H$_{41}$N$_2$O$_6$Cl; EI-MS m/z (%): 658 (M$^+_1$, 28), 656 (M$^+_2$, 96), 429 (100), 415 (54); IR (in KBr max): cm$^{-1}$: 1585. $^1$HNMR (200 MHz, CDCl$_3$) δ: 2.30 (s, N—CH$_3$), 2.68 (s, N'—CH$_3$), 3.20 (s, 7-OCH$_3$), 3.37 (s, 6'-OCH$_3$), 3.73 (s, 6-OCH$_3$), 3.91 (s, 12-OCH$_3$), 6.01 (s, 8'-H), 6.28 (dd, J=8.4, 2.0 Hz, 10'-H), 6.50 (s, 5'-H), 6.52 (s, 10-H), 6.79 (dd, j=8.2, 2.4 Hz, 11'-H), 6.86 (s, 13-H), 6.89 (s, 14-H), 7.13 (dd, J=8.4, 2.4 Hz, 13'-H), 7.34 (dd, J=8.2, 1.2 Hz, 14'-H). $^{13}$CNMR (75 MHz, CDCl$_3$) δ: 61.2 (1), 43.2 (3), 19.7 (4), 126.5 (4a), 120.7 (5), 147.0 (6), 143.0 (7), 147.1 (8), 127.9 (8a), 134.2 (9), 116.0 (10), 149.2 (11), 147.0 (12), 111.4 (13), 122.7 (14), 37.6 (15), 63.6 (1'), 45.0 (3'), 25.1 (4'), 126.6 (4a'), 112.1 (5'), 148.0 (6'), 143.2 (7'), 120.1 (8'), 127.9 (8a'), 134.8 (9'), 132.5 (10'), 121.8 (11'), 153.7 (12'), 121.8 (13'), 130.0 (14'), 41.2 (15'), 42.0 (N—CH$_3$), 42.4 (N'—CH$_3$), 55.3 (6-OCH$_3$), 56.0 (6'-OCH$_3$), 60.3 (12-OCH$_3$), 60.4 (7-OCH$_3$).

The following compounds were prepared by similar procedures.

Example 8

(8)

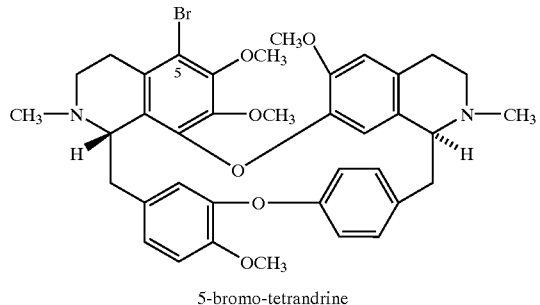

5-bromo-tetrandrine

Yield: 70%, A colorless needle crystalline (in methanol-ethyl ether); m. p.: 146–148°; C$_{38}$H$_{41}$N$_2$O$_6$Br; EI-MS m/z (%): 702 (M$^+_1$, 10), 700 (M$^+_2$), 473 (100), 476 (80); IR (in KBr max): cm$^{-1}$: 1520. $^1$HNMR (200 MHz, CDCl$_3$) δ: 2.28 (s, N—CH$_3$), 2.65 (s, N'—CH$_3$), 3.20 (s, 7-OCH$_3$), 3.39 (s, 6'-OCH$_3$), 3.72 (s, 6-OCH$_3$), 3.92 (s, 12-OCH$_3$), 6.03 (s, 8'-H), 6.29 (dd, J=8.2, 2.0 Hz, 10',14'-H), 6.49 (s, 5'-H), 6.79 (dd, j=8.4, 2.6 Hz, 11',13'-H), 6.87 (s, 10-H), 7.14 (dd, J=8.2, 2.2 Hz, 13'-H), 7.35 (dd, J=8.0, 2.0 Hz, 14-H). $^{13}$CNMR (75 MHz, CDCl$_3$) δ: 61.3 (1), 43.5 (3), 22.5 (4), 127.6 (4a), 112.5 (5), 148.2 (6), 142.6 (7), 147.5 (8), 127.8 (8a), 134.1 (9), 115.9 (10), 149.1 (11), 147.0 (12), 111.3 (13), 122.7 (14), 37.5 (15), 63.5 (1'), 44.8 (3'), 24.9 (4'), 127.6 (4a'), 112.0 (5'), 148.6 (6'), 143.1 (7'), 120.1 (8'), 127.9 (8a'), 134.6 (9'), 132.4 (10'), 121.7 (11'), 153.6 (12'), 121.7 (13'), 130.0 (14'), 41.2 (15'), 42.2 (N—CH$_3$), 41.9 (N'—CH$_3$), 55.2 (6-OCH$_3$), 55.9 (6'-OCH$_3$), 60.2 (12-OCH$_3$), 60.3 (7-OCH$_3$).

Example 9

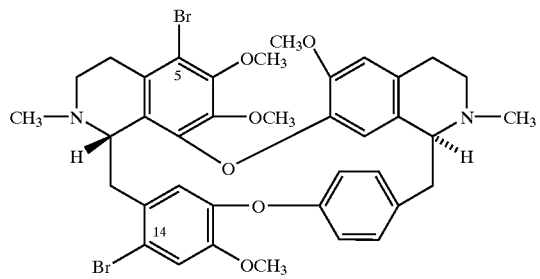

(9) 5,14-dibromo-tetrandrine

Yield: 73%, a colorless needle crystalline (in acetone-ethyl ether); m.p.: 184–185° C.; C$_{38}$H$_{40}$N$_2$O$_6$Br$_2$; EI-MS m/z (%): 782 (M$^+_1$, 18), 778 (M$^+_2$, 15); IR (in KBr max): cm$^{-1}$: 1586. $^1$HNMR (200 MHz, CDCl$_3$) δ: 2.27 (s, N—CH$_3$), 2.70 (s, N'—CH$_3$), 3.22 (s, 7-OCH$_3$), 3.37 (s, 6'-OCH$_3$), 3.72 (s, 6-OCH$_3$), 3.90 (s, 12-OCH$_3$), 6.01 (s, 8'-H), 6.32 (dd, J=8.2, 2.1 Hz, 10'-H), 6.53 (s, 5'-H), 6.56 (s, 10-H), 6.84 (dd, J=8.2, 2.4 Hz, 11'-H), 7.05 (s, 13-H), 7.05 (dd, J=8.0, 2.4 Hz, 13'-H), 7.35 (dd, J=8.4, 2.2 Hz, 14-H). $^{13}$CNMR (75 MHz, CDCl$_3$) δ: 61.8 (1), 44.0 (3), 23.0 (4), 127.3 (4a), 112.7 (5), 148.1 (6), 142.6 (7), 147.3 (8), 127.7 (8a), 133.4 (9), 115.7 (10), 148.9 (11), 147.3 (12), 115.6

(13), 127.3 (14), 37.4 (15), 63.3 (1'), 45.0 (3'), 25.1 (4'), 127.5 (4a'), 112.1 (5'), 148.8 (6'), 143.1 (7'), 119.8 (8'), 128.2 (8a'), 135.2 (9'), 132.3 (10'), 121.9 (11'), 121.6 (13'), 130.4 (14'), 39.8 (15'), 42.0 (N—CH$_3$), 42.3 (N'—CH$_3$), 55.3 (6-OCH$_3$), 56.1 (6'-OCH$_3$), 60.3 (12-OCH$_3$), 60.4 (7-OCH$_3$).

Example Nos. 10–15

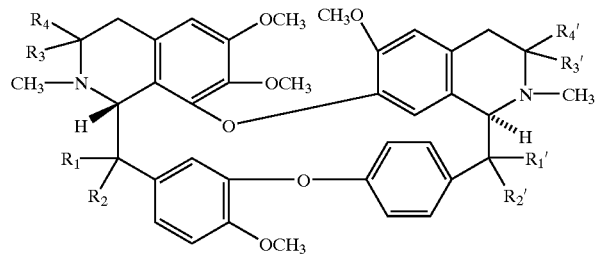

| Compound | R$_1$ + R$_2$ | R$_1$ + R$_2$ | R'$_1$ + R'$_2$ | R'$_1$ + R'$_2$ | Description | m.p. (° C.) | Yield (%) |
|---|---|---|---|---|---|---|---|
| NO. 10 | O | H H | O | H H | Colorless needle | 191–192 | 60 |
| NO. 11 | O | H H | H H | H H | Colorless needle | 210–211 | 55 |
| NO. 12 | H H | H H | O | H H | Colorless needle | 189–191 | 40 |
| NO. 13 | H H | O | H H | O | Colorless needle | 176–177 | 65 |
| NO. 14 | H H | O | H H | H H | Colorless needle | 194–195 | 45 |
| NO. 15 | H H | H H | H H | O | Amorphous powder |  | 30 |

Example Nos. 16–21

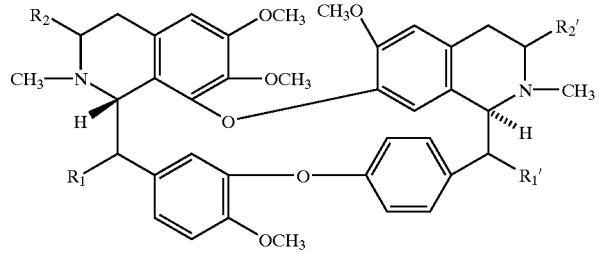

| Compound | R$_1$ | R$_2$ | R'$_1$ | R'$_2$ | Description | m.p. (° C.) | Yield (%) |
|---|---|---|---|---|---|---|---|
| NO. 16 | OCH$_3$ | H | OCH$_3$ | H | Colorless needle | 164–165 | 45 |
| NO. 17 | OCH$_3$ | H | H | H | Colorless needle | 179–181 | 55 |
| NO. 18 | H | H | OCH$_3$ | H | Colorless needle | 190–191 | 60 |
| NO. 19 | OAc | H | H | OCH$_3$ | Colorless needle | 197–198 | 65 |
| NO. 20 | H | OCH$_3$ | H | H | Colorless needle | 187–188 | 48 |
| NO. 21 | H | OAc | H | OAc | Colorless needle | 167–168 | 54 |

The structures of compounds described in the Example Nos. 1 to 21 were determined by spectral analyses. All compounds showed reddish-orange reaction with the potassium-bismuth iodide test solution.

Therapeutic Formulations

The following examples illustrate typical formulations comprising compounds of general formula (I), (referred to as Compound "X") for use in therapeutic treatment:

| (I): Tablet (1): | mg/tablet |
|---|---|
| Compound "X" | 100.0 |
| Lactose | 182.0 |
| Cross-link sodium carboxymethylcellulose | 12.0 |
| Starch | 2.25 |
| Magnesium stearate | 3.0 |
| (II): Tablet (2): | mg/tablet |
| Compound "X" | 20.0 |
| Avicel | 420.0 |
| Polyvinyl-pyrrolidone | 14.0 |
| Starch | 43.0 |
| Magnesium stearate | 3.0 |
| (III) Capsule: | mg/capsule |
| Compound "X" | 10.0 |
| Lactose | 488.5 |
| Magnesium stearate | 1.5 |
| (IV) Injection: | mg/2 mL |
| Compound "X" | 30.0 |
| Sodium sulfite | q.s. |
| Sodium Chloride | q.s. |

All publications, patents and patent applications mentioned in this specification are herein incorporated by reference into the specification in their entirety for all purposes.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

The foregoing is offered primarily for purposes of illustration. It will be readily apparent to those of ordinary skill in the art that the operating conditions, materials, procedural steps and other parameters of the invention described herein may be further modified or substituted in various ways without departing from the spirit and scope of the invention. For example, the invention has been described with human patients as the usual recipient, but veterinary use is also contemplated. Thus, the preceding description of the invention should not be viewed as limiting but as merely exemplary.

We claim:

1. A bis-isoquinoline alkaloid compound of formula (I) and salts thereof,

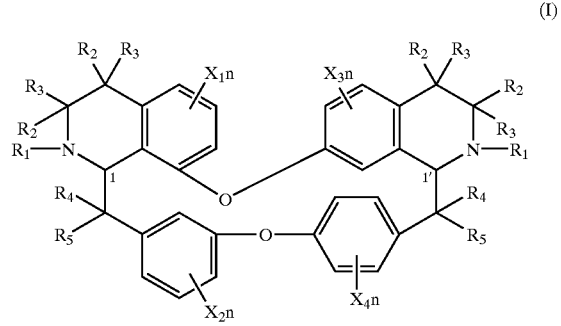

wherein:
   $R^1$ is hydrogen, straight chain or branched chain alkyl containing 1–10 carbon atoms;
   $R^2$ and $R^3$ are hydrogen, substituted acyl, straight chain or branched chain alkane in which the alkane is optionally interrupted by replacement with heterogeneous atoms O, N, or S, or $R^2$ and $R^3$ in combination comprise a ketone or thioketone;
   $R^4$ and $R^5$ are each selected from the group consisting of a hydrogen, a substituted acyl, a straight chain or branched chain alkyl in which the alkyl chain is optionally interrupted by replacement with a heterogeneous atom N or S, or $R^4$ and $R^5$ in combination consisting of a thioketone;
   $X_1$, $X_2$, $X_3$ and $X_4$ are same or different, and can be individually substituted by a halogen or substituted by straight or branched chain alkyloxy or acyloxy groups containing 1–10 carbon atoms, further wherein when $R^4$ and $R^5$ are both hydrogen, either (a) any one of $X_1$, $X_2$, $X_3$ and $X_4$ is a halogen or (b) $X_1$ is a straight or branched chain alkyloxy or acyloxy group, the alkyloxy group containing at least 3 carbon atoms;
   $C(1)$ and $C(1')$ are any possible combination of all stereoisomers of $C(1)$ and $C(1')$; and
   n is an integer between 1 and 4 for $X_2$, n is an integer between 0 and 4 for $X_4$, and n is an integer between 1 and 3 for $X_1$ and $X_3$.

2. The compound of claim 1, wherein the compound is selected from the group consisting of:
   7-propyloxy-fangchinoline, 7-n-butyloxy-fangchinoline, 7-isopropyloxy-fangchinoline, 7-isobutyloxy-fangchinoline, 7-propyl-acyloxy-fangchinoline, 7-butyl-acyloxy-fangchinoline, 5-chloro-tetrandrine, 5-bromo-tetrandrine, and 5,14-dibromo-tetrandrine.

3. A pharmaceutical composition for administration to a patient in need thereof, comprising:
   (a) a compound according to claim 1, or a pharmaceutically acceptable salt, ester, solvate or tautomer thereof; and
   (b) a pharmaceutically acceptable excipient or diluent.

4. The pharmaceutical composition of claim 3, further comprising:
   (c) an anti-cancer drug.

5. The pharmaceutical composition of claim 4, wherein the anti-cancer drug is selected from the group consisting of: microtubulin inhibitors, topoisomerase inhibitors, vinblastine, vincristine, vinorelbine, paclitaxel, docetaxel, colchicines analogs, harringtonine, homoharringtonine, camptothecine, camptothecine analogs and podophyllotoxin.

6. A method for enhancing anti-cancer chemotherapy comprising administration of an effective dose of a compound according to claim 1 in conjunction with anti-cancer chemotherapy.

7. A method for synergistically enhancing the effectiveness of one or more anti-cancer drugs comprising administration of an effective dose of a compound according to claim 1 in conjunction with one or more anti-cancer drugs.

8. A method for inhibiting multi drug resistance (MDR) comprising administration of an effective dose of a compound according to claim 1.

9. The method of claim 8, wherein the compound is selected from the group consisting of: 7-propyloxy-fangchinoline, 7-n-butyloxy-fangchinoline, 7-isopropyloxy-fangchinoline, 7-isobutyloxy-fangchinoline, 7-propyl-acyloxy-fangchinoline, 7-butyl-acyloxy-fangchinoline, 5-chloro-tetrandrine, 5-bromo-tetrandrine, and 5,14-dibromo-tetrandrine,

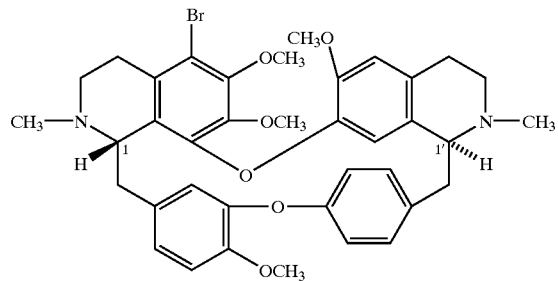

10. A method for increasing the intracellular concentration of an anti-cancer drug, the method comprising administration of an effective dose of a compound according to claim 1.

11. The method of claim 10, wherein the compound is selected from the group consisting of: 7-propyloxy-fangchinoline, 7-n-butyloxy-fangchinoline, 7-isopropyloxy-fangchinoline, 7-isobutyloxy-fangchinoline, 7-propyl-acyloxy-fangchinoline, 7-butyl-acyloxy-fangchinoline, 5-chloro-tetrandrine, 5-bromo-tetrandrine, and 5,14-dibromo-tetrandrine,

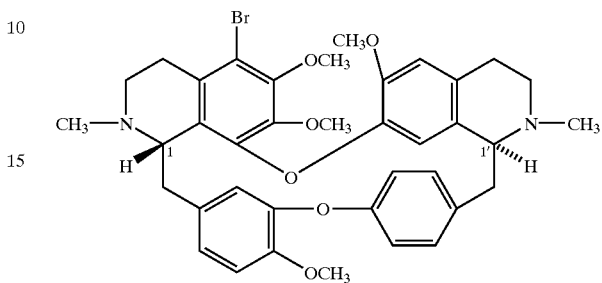

12. The method of claim 10, wherein the anti-cancer drug is selected from the group consisting of: microtubulin inhibitors, topoisomerase inhibitors, vinblastine, vincristine, vinorelbine, paclitaxel, docetaxel, colchicines analogs, harringtonine, homoharringtonine, camptothecine, camptothecine analogs and podophyllotoxin.

* * * * *